United States Patent
Vogt et al.

(10) Patent No.: US 10,293,078 B2
(45) Date of Patent: May 21, 2019

(54) POLYMETHYLMETHACRYLATE BONE CEMENT WITH ADJUSTABLE INITIAL VISCOSITY, AND METHOD FOR PRODUCING A BONE CEMENT DOUGH WITH VARIABLE INITIAL VISCOSITY

(71) Applicant: HERAEUS MEDICAL GMBH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 15/259,495

(22) Filed: Sep. 8, 2016

(65) Prior Publication Data
US 2017/0072093 A1 Mar. 16, 2017

(30) Foreign Application Priority Data
Sep. 10, 2015 (DE) .......................... 10 2015 217 315

(51) Int. Cl.
*A61L 24/06* (2006.01)
*A61L 24/04* (2006.01)
*A61L 24/00* (2006.01)

(52) U.S. Cl.
CPC ............ *A61L 24/06* (2013.01); *A61L 24/001* (2013.01); *A61L 24/043* (2013.01); *A61L 2430/02* (2013.01)

(58) Field of Classification Search
None
See application file for complete search history.

(56) References Cited

U.S. PATENT DOCUMENTS

| 4,900,546 A | * | 2/1990 | Posey-Dowty | ....... A61L 24/001 514/29 |
| 7,989,519 B2 | | 8/2011 | Vogt et al. | |

(Continued)

FOREIGN PATENT DOCUMENTS

| CN | 101217986 A | 7/2008 |
| CN | 101678148 A | 3/2010 |

(Continued)

OTHER PUBLICATIONS

Bone Cememt Matters, Simplex P Bone Cement (Year: 2008).*

(Continued)

*Primary Examiner* — Peter A Salamon
(74) *Attorney, Agent, or Firm* — Norris McLaughlin, P.A.

(57) ABSTRACT

A polymerizable polymethylmethacrylate bone cement, in which the initial viscosity of the cement dough can be controlled. The polymerizable bone cement composition comprises a monomer for radical polymerization, a powdered polymethylmethacrylate-co-polymer soluble in the monomer or a mixture comprising polymethylmethacrylate-co-polymers, a polymerization initiator, and a radiopaquer, wherein the powdered polymethylmethacrylate-co-polymer comprises at least one particulate polymethylmethacrylate-co-polymer having a molar mass of more than or equal to 200,000 g/mol, and the polymethylmethacrylate-co-polymer is obtainable by polymerization of a mixture of 90.0% or more by weight methylmethacrylate and 10.0% or less by weight of one or more comonomers, wherein the weight ratio of component A comprising the polymethylmethacrylate-co-polymer, radiopaquer, and polymerization initiator, and component B comprising a monomer for radical polymerization, stabilizer, and polymerization accelerator, is approximately 2.0 to 3.4 to 1.0, for controlling the initial (Continued)

viscosity of the bone cement dough formed by mixing components A and B.

21 Claims, 1 Drawing Sheet

(56) References Cited

U.S. PATENT DOCUMENTS

| | | | |
|---|---|---|---|
| 8,757,866 B2 | 6/2014 | Vogt et al. | |
| 8,834,845 B2 | 9/2014 | Nies et al. | |
| 9,387,275 B2 | 7/2016 | Vogt et al. | |
| 2004/0157954 A1* | 8/2004 | Imai | A61L 24/06 523/115 |
| 2009/0105144 A1* | 4/2009 | Vogt | A61L 24/0094 514/8.2 |
| 2009/0105367 A1* | 4/2009 | Vogt | A61L 24/001 523/116 |
| 2009/0105369 A1* | 4/2009 | Vogt | A61L 24/001 523/116 |
| 2009/0221730 A1 | 9/2009 | Kowalski et al. | |
| 2010/0228358 A1* | 9/2010 | Leonard | A61L 24/001 623/23.62 |
| 2010/0329074 A1* | 12/2010 | Vogt | A61B 17/8825 366/190 |
| 2011/0054392 A1 | 3/2011 | Nies | |
| 2011/0270259 A1 | 11/2011 | Shim | |
| 2016/0324559 A1 | 11/2016 | Vogt et al. | |

FOREIGN PATENT DOCUMENTS

| | | |
|---|---|---|
| CN | 102639157 A | 8/2012 |
| DE | 10 2007 050 763 A1 | 4/2009 |
| DE | 10 2007 050 768 A1 | 4/2009 |
| DE | 10 2007 052 116 A1 | 4/2009 |
| DE | 10 2009 031 178 B3 | 9/2010 |
| EP | 2 052 747 A2 | 4/2009 |
| EP | 2 055 324 A2 | 5/2009 |
| EP | 2 269 718 A2 | 1/2011 |
| EP | 3 093 067 A1 | 11/2016 |
| JP | S 6443261 A | 2/1989 |
| JP | 2004-008510 A | 1/2004 |
| JP | 2011-005255 A | 1/2011 |

OTHER PUBLICATIONS

English translation of Japanese Office Action corresponding to Japanese application No. 2016-176340, dated May 5, 2015.
European Search Report issued by the European Patent Office corresponds to EP Application No. 16187651.1, dated Feb. 3, 2017.
German Office Action for corresponding German Application No. 10 2015 217 315.1 dated Apr. 27, 2016.
English translation of European Office Action corresponding to European application No. 16187651.1, dated Jun. 19, 2018.
English Translation of Office Action and Search Report corresponds to Chinese Patent Application No. 201611009660.0 dated Dec. 27, 2018.

* cited by examiner

POLYMETHYLMETHACRYLATE BONE CEMENT WITH ADJUSTABLE INITIAL VISCOSITY, AND METHOD FOR PRODUCING A BONE CEMENT DOUGH WITH VARIABLE INITIAL VISCOSITY

The subject matter of the invention is a polymerisable polymethylmethacrylate bone cement, in which the initial viscosity of the cement dough can be controlled. The polymerisable bone cement corresponds to a composition comprising a monomer for radical polymerisation, a powdered polymethylmethacrylate-co-polymer that is soluble in the monomer or a mixture comprising polymethylmethacrylate-co-polymers that is soluble in the monomer, hereinafter referred to as polymethylmethacrylate-co-polymer, a polymerisation initiator, a radiopaquer, whereby the powdered polymethylmethacrylate-co-polymer comprises at least one particulate polymethylmethacrylate-co-polymer having a molar mass of more than or equal to 200,000 g/mol, and the polymethylmethacrylate-co-polymer can be obtained by polymerisation of a mixture of more than or equal to 90.0% by weight methylmethacrylate and less than or equal to 10.0% by weight of one or more comonomers, whereby the weight ratio of component A comprising at least one polymethylmethacrylate-co-polymer, one radiopaquer, and one polymerisation initiator, in particular dibenzoylperoxide, and component B comprising a monomer for radical polymerisation, a stabiliser, and a polymerisation accelerator, in particular an aromatic amine, is approximately 2.0 to 3.4:1.0, for controlling the initial viscosity of the bone cement dough that is formed by mixing the above-mentioned components A and B. A method for producing said bone cement and the use for adjustment of the variable initial viscosity as well as a kit for use in said method are also a subject matter of the invention.

BACKGROUND OF THE INVENTION

Polymethylmethacrylate (PMMA) bone cements are based on the pioneering work of J. Charnley (Charnley, J.: Anchorage of the femoral head prosthesis of the shaft of the femur. J. Bone Joint Surg. 42 (1960) 28-30.). PMMA bone cements consist of a liquid monomer component and a powder component. The monomer component generally contains the monomer, methylmethacrylate, and an activator dissolved therein. The powder component, also referred to as bone cement powder, comprises one or more polymers, such as PMMA, produced based on methylmethacrylate, a radiopaquer, and the initiator. Mixing the powder component and the monomer component, swelling of the polymers of the powder component in the methylmethacrylate generates a dough that can be shaped plastically and is the actual bone cement. The radical polymerisation of the methylmethacrylate is initiated by radicals that are formed during the mixing process. Upon advancing polymerisation of the methylmethacrylate, the viscosity of the cement dough increases until the cement dough solidifies.

Bone cements are subdivided into high viscosity, medium viscosity, and low viscosity bone cements, inter alia, according to the time until bone cement dough of the PMMA bone cements attains a tack-free condition (Kuhn, K.-D.: Knochenzemente für die Endoprothetik. Springer Verlag, 2001, 18-19.). High viscosity bone cements attain a tack-free condition after 1.0 to 1.5 min., whereas cements attaining a tack-free condition after 1.5 min to 3.0 min are referred to as medium viscosity cements. In low viscosity cements, the cement dough becomes tack-free after more than 3.0 min.

The term, "tack-free condition", is defined in ISO 5833 as the point in time, after the mixing of the cement powder with the monomer liquid, from which the cement dough surface can be touched with a gloved hand without the glove sticking to it.

The bone cement dough can be applied only once it attains a tack-free condition. This means that the point in time at which a tack-free condition is attained indicates the start of the processing phase of the polymethylmethacrylate bone cement. High viscosity and medium viscosity polymethylmethacrylate bone cements are used mainly in the mechanical fixation of large articular endoprostheses, for example of femoral and tibial components of knee-endoprostheses. Low viscosity polymethylmethacrylate bone cements are used with small articular endoprostheses, for example shoulder endoprostheses.

In all previously known cements, the adjustment of the initial viscosity is essentially done by means of specially composed and mutually matched cement powders that have a very well defined content of dibenzoyl peroxide.

The initial viscosity of the polymethylmethacrylate bone cement is reproducible under technical conditions over extended periods of time only with very sophisticated analytical efforts. To date, it is common with all industrially-produced polymethylmethacrylate bone cements that the manufacturer defines the initial viscosity of the polymethylmethacrylate bone cement by means of the composition of the cement powder. Thus far, the medical user has no way of adjusting the viscosity of the polymethylmethacrylate bone cement according to the user's needs during the surgery. In this regard, the specific composition of the known bone cements is limited to a fixed mixing ratio of monomers and powdered PMMA polymer component.

The invention is based on the object to develop a composition of a polymethylmethacrylate-co-polymer bone cement that allows a medical user to adjust the initial viscosity according to his or her needs by means of a single universal cement powder. It was another object to provide a method for application of the universally applicable bone cement as well as a kit that contains said universal cement powder and the monomer component and in which they can be applied directly.

The core of the invention is a specific, universally applicable powdered polymethylmethacrylate-co-polymer, in particular as a component A with a specific content of polymerisation initiator and a radiopaquer as well as, optionally, a pharmaceutically active substance that can be adjusted together with a monomer for radical polymerisation for producing bone cements with an initial viscosity ranging from low viscosity via medium viscosity to high viscosity.

SUMMARY OF THE INVENTION

The invention is based on finding, surprisingly, that, using the bone cement powder composed according to the invention, varying the weight ratio of cement powder (component A) and monomer liquid (component B) allows the initial viscosity of the cement dough formed from the cement powder and the monomer liquid to be adjusted in specific manner. Accordingly, there is no need for cement powders with a special composition for each viscosity. Accordingly, the composition according to the invention saves the user the purchase of a number of products that are currently needed for adjusting a specific viscosity, because the user is now enabled to adjust the entire range of desired bone cement viscosities right during the processing using a single product.

The subject matter of the invention is a composition for use as polymerisable bone cement, in particular a polymerisable bone cement comprising
(i) at least one monomer for radical polymerisation, in particular at least methylmethacrylate;
(ii) at least one powdered polymethylmethacrylate-co-polymer or mixtures comprising polymethylmethacrylate-co-polymers that is/are soluble in (i);
(iii) at least one polymerisation initiator, in particular 0.6 to 2.5% by weight, preferably 0.8 to 2.5% by weight, preferably 0.8 to 2.0% by weight relative to the total composition being 100% by weight, preferably 0.6 to 0.8 to 1.4 to 1.95% by weight dibenzoylperoxide relative to the total composition, particularly preferably 0.65 to 1.92% by weight relative to the total composition;
(iv) at least one radiopaquer, whereby
the (ii) powdered polymethylmethacrylate-co-polymer comprises at least one particulate polymethylmethacrylate-co-polymer having a molar mass Mn of more than or equal to 200,000 g/mol to 1,000,000 g/mol, in particular up to 500,000 g/mol, and the polymethylmethacrylate-co-polymer can be obtained by polymerisation of a mixture of more than or equal to 90.0% by weight methylmethacrylate and less than or equal to 10.0% by weight of one or more comonomers, which, in particular, do not correspond to methylmethacrylate, and the total composition of the polymethylmethacrylate-co-polymer or of mixtures containing at least one co-polymer is 100% by weight relative to said mixture, whereby the composition can be obtained by
mixing two components A and B,
whereby component A is present as a powder and comprises
(a.1) at least one powdered polymethylmethacrylate-co-copolymer or mixtures comprising at least one polymethylmethacrylate-co-polymer;
(a.2) at least one powdered radiopaquer; and
(a.3) at least one polymerisation initiator; in particular dibenzoylperoxide; and component B is present as a liquid and comprises
(b.1) at least one monomer for radical polymerisation;
(b.2) optionally, at least one polymerisation accelerator, in particular aromatic amine, preferably N,N-dimethyl-p-toluidine; and
(b.3) optionally, at least one stabiliser,
whereby the weight ratio of component A comprising the powdered polymethylmethacrylate-co-polymer and component B comprising the monomer for radical polymerisation ranges from approximately 2.0 to 3.4:1.0, whereby the weight ratio of component A and component
B is selected from
a) less than 2.2:1.0, or
b) from 2.2 to less than 3.3:1.0, or
c) from more than or equal to 3.3:1.0.
In this context, it is particularly preferred to have components A and B be present at a weight ratio of a) less than 2.2:1.0, in particular 2.0 to less than 2.2:1.0, or b) from 2.2 to less than 3.3:1.0, in particular from more than 2.2 to 3.2:1.0, or c) from more than or equal to 3.3:1.0, in particular from 3.3 to less than 3.4:1.0, whereby, in particular, component A comprises 1.0:2.5% by weight of at least one polymerisation initiator, in particular dibenzoylperoxide relative to the total composition of component A being 100% by weight.

DETAILED DESCRIPTION

Preferred comonomers comprise styrene, ethylacrylate, methylacrylate or mixtures containing at least two of said comonomers. The powdered polymethylmethacrylate-co-polymers are preferably produced in an emulsion polymerisation. Particularly preferably, at least one comonomer selected from at least one alkylacrylate with 1 to 5 C-atoms in the alkyl group, in particular methylacrylate, ethylmethacrylate, phenylalkylene with 8 to 20 C-atoms, in particular phenylethene (styrene), diene, in particular 1,3-butadiene or isoprene, and/or a mixture containing at least one of said comonomers, is polymerised with methylmethacrylate. The molar mass of the polymethylmethacrylate polymer specified above corresponds to the number average of the molar mass $M_n$, which can be determined by means of GPC analysis, which is familiar to a person skilled in the art.

According to the invention, hereinafter the powdered polymethylmethacrylate-co-polymer or mixtures comprising polymethylmethacrylate-co-polymers are summarily referred to as powdered polymethylmethacrylate-co-polymer such that the co-polymer shall be understood to also include mixtures comprising at least one polymethylmethacrylate-co-polymer.

According to the invention, it is particularly preferred to have the weight ratio of the polyacrylate (ii), the radiopaquer, and the polymerisation initiator to the monomer for radical polymerisation (i) and, optionally, to the polymerisation accelerator be from approximately 2.0 to 3.4 to 1.0. The specific adjustment of said weight ratio for producing the polymerisable bone cement allows for the specific adjustment of the initial viscosity of the obtainable bone cement dough.

Accordingly, a subject matter of the invention is a polymerisable bone cement, whereby the bone cement is present as a) low viscosity bone cement, in particular with a tack-free condition according to ISO 5833 being attained after more than 3.0 minutes after the mixing, or as b) medium viscosity bone cements, in particular with a tack-free condition according to ISO 5833 being attained after from more than or equal to 1.5 to 3.0 minutes after the mixing, or as c) high viscosity bone cements, in particular with a tack-free condition according to ISO 5833 being attained after more than or equal to 1.0 to less than 1.5 minutes after the mixing.

The initial viscosity of the bone cement is defined by the period of time that elapses between the mixing of the components to the attainment of a tack-free condition by the bone cement. Accordingly, the initial viscosity of a cement in tack-free condition according to ISO 5833 after more than 3.0 minutes is classified to be low viscosity, where as the initial viscosity is classified to be medium viscosity if the tack-free condition according to ISO 5833 is attained after more than or equal to 1.5 to 3.0 minutes after the mixing, and the initial viscosity is a high viscosity if the tack-free condition according to ISO 5833 is attained after more than or equal to 1.0 to 1.5 minutes.

When the powder component is being mixed with the monomer component, the polymerisation accelerator, in particular N,N-dimethyl-p-toluidine reacts with the polymerisation initiator dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Surprisingly, the bone cement according to the invention allows for adjustment of the flexural strength [MPa], flexural modulus [MPa] and/or compressive strength [MPa] of the fully polymerised cured bone cements that were mixed at a weight ratio of component A to component B of 2.0 to 3.4 to 1.0, measured according to ISO 5833, to a flexural strength of 78 to 90 MPa, in particular of 79 to 88 MPa, and/or to a flexural modulus of 3,100 to 3,700 MPa, in particular from 3,150 to 3,600 MPa, and/or to a compressive strength of 100 to 113 MPa, in particular of 105 to 114 MPa. Accordingly, bone cements whose quality clearly exceeds the requirement of ISO 5833, can be produced with the composition according to the invention.

According to the invention, a specific content of polymerisation initiator in component A or in the above-mentioned composition is adjusted in order to produce the universally usable component A and/or the composition comprising components (ii), (iii), and (iv). It is particularly preferred in this context that the content of polymerisation initiator is from 1.0 to 2.5% by weight, in particular 1.0 to 2.5% by weight dibenzoylperoxide, in particular relative to 100% by weight relative to component A or components (ii), (iii), and (iv), in the composition comprising components (ii), (iii), and (iv) or component A.

According to further variants of embodiments, the monomer for radical polymerisation comprising at least methylmethacrylate and at least one further monomer can be selected from an alkyl-2-acrylic acid alkylester, aryl-2-acrylic acid alkylester, arylalkyl-2-acrylic acid alkylester, each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, or a mixture comprising at least two of said monomers.

According to a particularly preferred embodiment, a composition according to the invention for use as a polymerisable bone cement or for use in the method according to the invention, in particular comprising a pharmaceutically active substance, comprises two components A and B, whereby component A is present as a powder and comprises
(a.1) 75 to 85% by weight of at least one powdered polymethylmethacrylate-co-polymer or of a mixture comprising at least one polymethylmethacrylate-co-polymer selected from a particulate polymethylmethacrylate-co-polymer with a molar mass Mn of more than or equal to 200,000 g/mol, in particular up to 1,000,000 g/mol, preferably 800,000 g/mol, particularly preferably 300,000 g/mol, whereby the polymethylmethacrylate-co-polymer can be obtained by polymerisation of a mixture of more than or equal to 90.0% by weight methylmethacrylate and less than or equal to 10.0% by weight of one or more comonomers that do not correspond to methylmethacrylate, and the total composition accounts for 100% by weight relative to said mixture;
(a.2) 10 to 20% by weight, in particular 12 to 16% by weight, of at least one powdered radiopaquer, in particular zirconium dioxide; and
(a.3) 1.0 to 2.5% by weight of at least one polymerisation initiator, in particular dibenzoylperoxide;
(a.4) 0.0 to 10% by weight of at least one pharmaceutically active substance, in particular from 0.5 to 5.0% by weight; whereby, in particular the pharmaceutically active substance is at least one antibiotic, such as an aminoglycoside antibiotic, preferably a pharmaceutically effective salt of gentamicin, such as gentamicin sulfate, tobramycin, vancomycin, clindamycin, erythromycin, colistin and/or the pharmacologically tolerable salts thereof;
whereby the total composition of the components adds up to 100% by weight; and component B is present as a liquid and comprises (b.1) 95 to 99% by weight, in particular 97.5 to 99% by weight, of at least one monomer for radical polymerisation, in particular methyl methacrylate;
(b.2) 0.1 to 5% by weight, in particular 1.0 to 2.5% by weight, of at least one polymerisation accelerator, in particular an aromatic amine, preferably N,N-dimethyl-p-toluidine; and
(b.3) 0 to 2.0% by weight of at least one stabiliser such as hydroquinone, and (b.4) optionally, a content of a colourant such as chlorophyllin E141, in particular 0 to 100 ppm by weight,
whereby the total composition of components B adds up to 100% by weight, and whereby, in particular, the weight ratio of component A comprising the powdered polymethylmethacrylate-co-polymer or a mixture comprising at least one polymethylmethacrylate-co-polymer, preferably a mixture of polymethylmethacrylate-co-polymers, and component B comprising the monomer for radical polymerisation is from approximately 2.0 to 3.4:1.0, particularly preferably the weight ratio corresponds to a), b) or c).

Component A can contain, as pharmaceutically active substance, at least one antibiotic, antimycotic agent, antiseptic agent, antiphlogistic agent, at least one growth factor, and at least one bisphosphonate. Preferred antibiotics comprise gentamicin, tobramycin, amikacin, vancomycin, teicoplanin, ramoplanin, dalbavancin, daptomycin, fosfomycin, clindamycin and/or lincomycin. In this context, amphotericin B and caspofungin are preferred as antimycotic agents.

According to a further preferred embodiment, the particle size of the powdered polymethylmethacrylate-co-polymer particles can be less than or equal to 100 μm, in particular, the particle size $d_{99}$ of the particles is less than or equal to 100 μm, in particular less than 100 μm to 1 μm.

According to a further preferred embodiment, the composition according to the invention can contain at least one monomer having adsorption groups. An adsorption group can, for example, be an amide group. Accordingly, the monomer with adsorption group can, for example, be methacrylic acid amide. Using at least one monomer with adsorption groups allows the binding of the bone cement to articular endoprostheses to be influenced specifically.

According to a particularly preferred alternative, the composition according to the invention comprises, in particular before the polymerisation, as powdered component A, at least one polymethylmethacrylate polymer, one radiopaquer, and dibenzoylperoxide and contains, separately, as liquid component B polymerisable monomer, methylmethacrylate, a stabiliser, and at least one aromatic amine, whereby component A comprises a) at least one particulate polymethylmethacrylate-co-polymer with a molar mass Mn of more than 200,000 g/mol to 1,000,000 g/mol, whereby the polymethylmethacrylate-co-polymer was produced by polymerisation of a mixture of more than or equal to 90.0% by weight methylmethacrylate and less than or equal to 10.0% by weight of one or more comonomers; and b) 1.0 to 2.5% by weight dibenzoylperoxide;
wherein the weight ratio of component A to component B is varied from 2.0 to 3.4 to 1.0 in order to control the initial viscosity of the cement dough that is formed by mixing the cement powder with the monomer liquid.

Another subject matter of the invention is a method for producing a bone cement dough that has variable initial viscosity. According to the method according to the invention, component A and/or components (ii), (iii), and (iv) are mixed with component B and/or component (i) and at least one polymerisation initiator at a weight ratio of 2.0 to 3.4:1.0 in order to adjust the initial viscosity of the obtainable polymethylmethacrylate bone cement. In the method according to the invention, the weight ratio during the mixing process is alternatively a) less than or equal to 2.2:1.0, or b) from 2.2 to less than 3.3:1.0, or c) from more than or equal to 3.3:1.1 for the production of polymerisable bone cements.

The variation of the amount of monomer liquid can be effected by means of a suitable dosing facility such as, for example, an automatic pipette, or suitable full-prepacked mixing systems, as described in application DE102015106899.0 (priority as of Apr. 5, 2015 with the German Patent Office, DPMA). Said full-prepacked mixing system is equipped with a device for adjustable dosing of the amount of monomer liquid by means of which the weight ratio of cement powder and monomer liquid can be varied.

Another subject matter of the invention is a method for producing a polymerisable bone cement by mixing two components A and B with each other, whereby component A is present as a powder and comprises (a.1) at least one powdered polymethylmethacrylate-co-polymer, whereby the polymethylmethacrylate-co-polymer comprises at least one particulate polymethylmethacrylate-co-polymer with a molar mass Mn of more than or equal to 200,000 g/mol to 1,000,000 g/mol, whereby the polymethylmethacrylate-co-polymer can be obtained by polymerisation of a mixture of more than or equal to 90.0% by weight methylmethacrylate and less than or equal to 10.0% by weight of one or more comonomers, and the total composition accounts for 100% by weight relative to said mixture, (a.2) at least one powdered radiopaquer, and (a.3) at least one polymerisation initiator: and component B is present as a liquid and comprises (b.1) at least one monomer for radical polymerisation, in particular at least methylmethacrylate, (b.2) at least one polymerisation accelerator, and (b.3) at least one stabiliser, whereby the weight ratio of component A comprising the polymethylmethacrylate-co-polymer and component B comprising the monomer for radical polymerisation is from approximately 2.0 to 3.4 to 1.0, whereby, in particular, component A comprises from 1.0 to 2.5% by weight of at least one polymerisation initiator, in particular dibenzoylperoxide, relative to the total composition of component A accounting for 100% by weight. Components A and B are always present as corresponding total composition accounting for 100% by weight.

According to particularly preferred variants of the method, component A and component B are mixed at a weight ratio of a) less than 2.2 to 1.0 or b) from 2.2 to less than 3.3 to 1.0, in particular from more than 2.2 to 3.2 to 1.0, or c) from more than or equal to 3.3 to 1.0, in particular from 3.3 to 3.4 to 1.0, in order to produce polymerisable bone cements and, in particular, to control the initial viscosity of the polymerisable bone cements via the mixing ratio.

According to a further particularly preferred variant, component A and component B can be mixed at a weight ratio of a) less than 2.2 to 1.0, in particular from 2.0 to less than 2.2 to 1.0, in order to produce low viscosity bone cements attaining a tack-free condition according to ISO 5833 after more than 3.0 minutes after the mixing, or b) from 2.2 to less than 3.3 to 1.0, in particular from more than 2.2 to 3.2 to 1.0, in order to produce medium viscosity bone cements attaining a tack-free condition according to ISO 5833 after from more than or equal to 1.5 to 3.0 minutes after the mixing, or c) from more than or equal to 3.3 to 1.0, in particular from 3.3 to 3.4 to 1.0, in order to produce high viscosity bone cements attaining a tack-free condition according to ISO 5833 after more than or equal to 1.0 to less than 1.5 minutes after the mixing.

According to the invention, it is preferred that the method involves the dosing of component A and component B at a weight ratio corresponding to a), b) or c) to take place by means of dosing the corresponding volume of components A and B as calculated from the weight ratio, for example in milliliters or liters.

According to a further preferred alternative, a method is claimed, in which a defined amount of component A, in grams, for attaining the weight ratio a), b) or c) or a volume of component A corresponding to said amount is provided in the internal space of a cartridge, whereby the cartridge comprises a cartridge connector on one of its ends and a dispensing plunger on its other, opposite end, whereby a mixing rod can be attached to or is arranged on a mixing facility on the inside of the cartridge through a feed-through, whereby the mixing facility can be operated from outside by moving the mixing rod along an axis of the internal space, whereby, optionally, a connecting conduit is allocated to the cartridge and component B is provided in a disposable monomer container. The connecting conduit can be allocated to the cartridge connector either indirectly or directly.

Moreover, the method preferably comprises the steps of: transferring a defined amount of component B, in grams, for attaining the weight ratio a), b) or c) or a corresponding volume of component B from the disposable monomer container to the cartridge, in particular by means of a dosing facility and, optionally, a connecting conduit, and mixing of components A and B.

Moreover, according to the invention, mixing component A and component B at a weight ratio of a) less than 2.2 to 1.0 leads to low viscosity bone cements attaining a tack-free condition according to ISO 5833 after more than 3.0 minutes after the mixing being obtained, or b) of 2.2 to less than 3.3 to 1.0 leads to medium viscosity bone cements attaining a tack-tree condition after ISO 5833 after from more than or equal to 1.5 to 3.0 minutes after the mixing being obtained, or c) of more than or equal to 3.3 to 1.0 leads to high viscosity bone cements attaining a tack-free condition after ISO 5833 after more than or equal to 1.0 to less than 1.5 minutes after the mixing being obtained.

According to a further particularly preferred variant of the method, component A and component B are mixed in the internal space by means of a mixing facility by operating the mixing facility by moving a mixing rod that extends into the internal space of the cartridge and can be rotated and can be shifted in longitudinal direction, whereby it is preferred to pull the mixing rod out of the internal space of the cartridge up to the limit stop after the mixing and it is particularly preferred to break off the mixing rod at a predetermined breakage site after pulling it out to the limit stop.

According to a further particularly preferred variant of the method, the cartridge containing the low viscosity, medium viscosity or high viscosity polymerisable bone cement is being detached from the connecting conduit and, optionally, a cartridge bracket and the bone cement is dispensed from the internal space of the cartridge by propelling a dispensing plunger that is supported such as to be axially mobile in the cartridge and forms a boundary of the internal space of the cartridge on one side.

Also a subject matter of the invention is a kit for producing polymerisable bone cements comprising components A and, optionally, component B, whereby component A is present as a powder and comprises (a.1) at least one powdered polymethylmethacrylate-co-polymer, whereby the powdered polymethylmethacrylateco-polymer comprises at least one particulate polymethylmethacrylate-co-polymer with a molar mass Mn of more than or equal to 200,000 g/mol to 1,000,000 g/mol, and the polymethylmethacrylate-co-polymer can be obtained by polymerisation of a mixture of more than or equal to 90.0% by weight methylmethacrylate and less than or equal to 10.0% by weight to more than or equal to 1% by weight of one or more comonomers, and the total composition accounts for 100% by weight relative to said mixture;
(a.2) at least one powdered radiopaquer; and
(a.3) at least one polymerisation initiator; and component B is present as a liquid and comprises
(b.1) at least one monomer for radical polymerisation;
(b.2) optionally, at least one polymerisation accelerator; and
(b.3) optionally at least one stabiliser; and
whereby component A is present in the internal space of a cartridge, whereby cartridge 1 comprises a cartridge connector with internal thread 8 on one of its ends and a dispensing plunger 2 on its other, opposite end, whereby a mixing rod 4 can be attached to or is arranged on a mixing facility on the inside 13 of the cartridge through a feedthrough, whereby the mixing facility can be operated from outside by moving the mixing rod 4 along an axis of the internal space, and, optionally, component B, whereby component B is contained in a disposable or reusable monomer container (vial), in particular component B is present in a glass ampoule with an ampoule head that can be broken off.

According to an alternative, the glass ampoule, the cartridge and/or a dosing facility that is arranged between the monomer container and the cartridge comprise markings. Alternatively, the mixing rod or a cartridge window can also comprise markings. The markings allow the amount of component B to be added to attain the weight ratio, or the volume ratio, that corresponds to the weight ratio, of component A comprising the polymethylmethacrylate-co-polymer to component B comprising the monomer for radical polymerisation of approximately 2.0 to 3.4:1.0 to be read from the scale division of the marking. Alternatively or in addition, the markings can preferably be present as snap-in elements, for example inside the cartridge and/or on the dosing facility, to which corresponding markings are allocated, for example on the outside of the cartridge, for example in the form of labelling specifying the information concerning the weight ratio, volume ratio, or the adjusted viscosity.

Particularly preferably, the dosing facility is allocated to the monomer container and the connecting conduit of the cartridge such that the monomer exiting from the monomer container can be transferred into the dosing facility and can be transferred from there into the cartridge according to the desired mixing ratio. The dosing facility preferably comprises a hollow cylindrical body with an axially shiftable plunger. The monomer can flow into or be taken up by the hollow cylinder. The transfer of the monomer and the dosing of the monomer into the cartridge can take place by means of snap-in elements in the hollow cylinder and/or on the axial shiftable plunger.

It is particularly preferred to provide snap-in elements on the dosing facility and/or markings in a cartridge window that indicate an addition as weight ratio of component B for attaining the weight ratio of component A comprising the polymethylmethacrylate-co-polymer and component B. According to the invention, the cartridge comprises a mixing chamber.

According to a further particularly preferred alternative, the dispensing plunger 2 for component A is impermeable, preferably a pore filter that is permeable for gas and impermeable for component B is arranged in the dispensing plunger 2.

Another subject matter of the invention is a polymerisable bone cements that can be obtained by mixing and polymerising component A and B according to the method according to the invention or by mixing components A and B of the kit or by mixing components (i), (ii), (iii), (iv) as well as, optionally, a polymerisation accelerator.

According to a particularly preferred embodiment, a subject matter of the invention is the use of a composition comprising component A and B or of the composition that can be obtained according to the method according to the invention or the kit for production thereof, in particular for variable adjustment of the initial viscosity of bone cements from low to medium to high viscosity, in particular of a) low viscosity bone cements by mixing component A and component B at a weight ratio of less than 2.2 to 1.0, whereby the bone cements attain a tack-free condition according to ISO 5833 after more than 3.0 minutes after the mixing, or b) medium viscosity bone cements by mixing component A and component B at a weight ratio from 2.2 to less than 3.3 to 1.0, whereby the bone cements attain a tack-free condition according to ISO 5833 after more than or equal to 1.5 to 3.0 minutes after the mixing, or c) high viscosity bone cements by mixing component A and component B at a weight ratio of more than 3.3, whereby the bone cements attain a tack-free condition according to ISO 5833 after more than or equal to 1.0 to less than 1.5 minutes after the mixing.

According to a further embodiment, a subject matter of the invention is a polymerised cured bone cement, in particular in the form of a three-dimensional moulded body, preferably of a surgical implant or part thereof. Another subject matter of the invention is an implant for use as surgical implant or part of an implant, revision implant, screw, nail, surgical plate, for mechanical fixation of primary total articular endoprostheses, for mechanical fixation of revision total articular endoprostheses, for augmentation of osteoporotic bone tissue and, particularly preferably, for vertebroplasty, kyphoplasty, and augmentation of drill holes in osteoporotic bone tissue, for filling bone cavities, for femuroplasty, for the manufacture of spacers, for mechanical fixation of articular endoprostheses, for covering skull defects or for the production of carrier materials for local antibiotics therapy, as femoral and tibial components of knee endoprostheses, as shoulder endoprostheses or as carrier material for local release of pharmaceutically active substances. The implants or products mentioned above are also a subject matter of the invention. According to an alternative, a subject matter of the invention is a composition, a kit for a surgical implant consisting of the bone cement cured according to the invention for use in the augmentation of osteoporotic bone tissue and, particularly preferably, in vertebroplasty, kyphoplasty, and augmentation of drill holes in osteoporotic bone tissue, for filling bone cavities, for femuroplasty, for the manufacture of spacers, for mechanical fixation of articular endoprostheses, for covering skull defects or for the production of carrier materials for local antibiotics therapy, as carrier material for local release of pharmaceutically active substances.

According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

Radiopaquers can preferably be selected from the group consisting of metal oxides, such as, in particular, zirconium dioxide, barium sulfate, toxicologically acceptable heavy metal particles, such as, for example, tantalum, ferrite, magnetite (supramagnetic magnetite also, if applicable), and biocompatible calcium salts. Said radiopaquers preferably have a mean particle diameter in the range of 10 nm to 500 μm. Moreover, conceivable radiopaquers also include esters of 3,5-bis(acetamido)-2,4,6-triiodobenzoic acid, gadolinium compounds, such as gadolinium chelate involving the esters of 1,4,7,10-tetraazacyclododecane-1,4,7,10-tetraacetic acid (DOTA). The radiopaquer content, in particular the zirconium dioxide concentration, in component A can, each independent of each other, be in the range of, for example, 3 to 30% by weight relative to the corresponding total composition.

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve in the polymerisable monomer at a temperature of 25° C.

According to the invention, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide.

The barbituric acid derivative preferably is a barbituric acid derivative selected from the group consisting of 1-mono-substituted barbiturates, 5-mono-substituted barbiturates, 1,5-di-substituted barbiturates, and 1,3,5-tri-substituted barbiturates. According to a particular refinement of the invention, the barbituric acid derivative is selected from the group consisting of 1,5-di-substituted barbiturates and 1,3,5-tri-substituted barbiturates.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred. According to a preferred embodiment, the substituents each have a length of 1 to 10 carbon atoms, more preferably a length of 1 to 8 carbon atoms, and particularly preferably a length in the range of 2 to 7 carbon atoms. According to the invention, barbiturates bearing one substituent each at position 1 and position 5 or one substituent each at positions 1, 3, and 5 are preferred. According to another preferred embodiment, the barbituric acid derivative is a 1,5-disubstituted barbiturate or a 1,3,5-trisubstituted barbiturate. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator. Heavy metal compounds that are preferred according to the invention are selected from the group consisting of copper(II) hydroxide, copper(II) methacrylate, copper(II) acetylacetonate, copper (II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two thereof.

According to another embodiment of the composition according to the invention, the polymerisation accelerator is selected from the group consisting of aromatic amines, such as, in particular, N,N-dimethyl-p-toluidine, N,N-bis-hydroxyethyl-p-toluidine, N,N-dimethyl-aniline, phthalimide, succinimide, pyromelithic acid diimide, and a mixture of at least two thereof.

Another advantageous refinement of the invention comprises a use of combinations of heavy metal salts and at least one member from the group comprising N,N-dimethyl-p-toluidine, N,N-bis-hydroxyethyl-p-toluidine, N,N-dimethyl-aniline as polymerisation accelerator. In this context, combinations of two and combinations of three different polymerisation accelerators are disclosed in the scope of the invention.

An advantageous refinement of the invention consists of the composition according to the invention or any of the components A or B containing at least one polymerisation co-accelerator, if applicable, whereby tertiary amines and amidines are preferred as polymerisation co-accelerators, and whereby N,N-dimethyl-p-toluidine, N,N-bis-hydroxyethyl-p-toluidine, N,N-dimethyl-anilin, are preferred as co-accelerators.

The polymethylmethacrylate bone cement according to the invention can be used for mechanical fixation of primary articular endoprostheses and for anchoring revision articular endoprostheses. The polymethylmethacrylate bone cement can just as well be used for the production of spacers and local active substance carriers. It is also possible to cover bone defects on the skull bone with the polymethylmethacrylate bone cement according to the invention.

The invention is illustrated through the examples presented in the following, though without limiting the scope of the invention to said examples.

A polymethylmethacrylate-co-methylmethacrylate with a number average molar mass of more than 200,000 g/ml produced by suspension polymerisation was used for the cements of examples (a-j). These copolymers were produced from a mixture of methylmethacrylate and methylacrylate, whereby the methylmethacrylate content was more than 90% by weight and the methylacrylate content was less than 10% by weight. The sieve fraction below 100 μm of the polymer beads of the polymethylmethacrylate-co-methylmethacrylate was used. Commercial dibenzoylperoxide phlegmatised with water was used as initiator. Commercial zirconium dioxide was used as radiopaquer.

Composition of component A as cement powder 1:
15.0 wt. % zirconium dioxide
2.0 wt. % dibenzoylperoxide
83.0 wt. % polymethylmethacrylate-co-methylmethacrylate The composition of component B synonymous to monomer liquid was as follows: 98 wt. % methylmethacrylate, 2.0 wt. % N,N-dimethyl-p-toluidine, traces of chlorophyllin E141, stabilised with ~40 ppm hydroquinone The test of the processing properties of cements (a-e) was done in accordance with ISO 5833.

| Cement | Weight ratio of cement powder and monomer liquid | Mixing time | Tack-free condition [min] | End of processing |
|---|---|---|---|---|
| a | 2.1:1.0 | 30 s | 3 min 0 s | 5 min 10 s |
| b | 2.4:1.0 | 30 s | 2 min 29 s | 4 min 40 s |

| Cement | Weight ratio of cement powder and monomer liquid | Mixing time | Tack-free condition [min] | End of processing |
|---|---|---|---|---|
| c | 2.6:1.0 | 30 s | 2 min 10s | 4 min 5 s |
| d | 2.9:1.0 | 30 s | 1 min 45 s | 3 min 58 s |
| e | 3.2:1.0 | 30 s | 1 min 35 s | 3 min 45 s |

Cement (a) is a low viscosity cement. Cements (b), (c) and (d) are medium viscosity cements. Cement (e) is a high viscosity cement.

Strip-shaped test bodies sized 3.3 mm×10.0 mm×75 mm were produced for the determination of flexural strength and flexural modulus of cements (a-e) in accordance with ISO 5833. Cylinder-shaped test bodies with a diameter of 6 mm and a height of 10 mm were produced for the determination of the compressive strength. A Zwick Z010 universal testing apparatus was used in the determination of the flexural strength, flexural modulus, and compressive strength in accordance with ISO 5833.

| Cement | Weight ratio of cement powder and monomer liquid | Flexural strength [MPa] | Flexural modulus [MPa] | Compressive strength [MPa] |
|---|---|---|---|---|
| a | 2.1:1.0 | 80.3 ± 1.2 | 3246 ± 94 | 107.1 ± 2.2 |
| b | 2.4:1.0 | 81.8 ± 1.3 | 3277 ± 107 | 109.6 ± 1.6 |
| c | 2.6:1.0 | 79.7 ± 0.8 | 3177 ± 55 | 113.3 ± 0.6 |
| d | 2.9:1.0 | 81.6 ± 1.6 | 3267 ± 68 | 112.1 ± 1.4 |
| e | 3.2:1.0 | 85.8 ± 2.2 | 3510 ± 162 | 112.6 ± 1.7 |

ISO 5833 requires a flexural strength in excess of 50 MPa, a flexural modulus in excess of 1,800 MPa, and a compressive strength in excess of 70 MPa. The cements of examples (a-e) meet the requirements of ISO 5833 with regard to the flexural strength, flexural modulus, and compressive strength.

In addition, a gentamicin-containing component A2 was produced as a cement powder 2.

Composition of cement powder 2 containing added gentamicin sulfate:

14.4 wt. % zirconium dioxide
1.8 wt. % dibenzoylperoxide
79.7 wt. % polymethylmethacrylate-co-methylmethacrylate
4.1 wt. % gentamicin sulfate (equivalent to 2.5 wt. % gentamicin base)

The composition of the monomer liquid was as follows: 98 wt. % methylmethacrylate, 2.0 wt. % N,N-dimethyl-p-toluidine, traces of chlorophyllin E141, stabilised with ~100 ppm hydroquinone The test of the processing properties of cements a-e was done in accordance with ISO 5833.

| Cement | Weight ratio of cement powder 2 and monomer liquid | Mixing time | Tack-free condition [min] | End of processing |
|---|---|---|---|---|
| f | 2.2:1.0 | 30 s | 3 min 20 s | 5 min 32 s |
| g | 2.5:1.0 | 30 s | 2 min 40 s | 4 min 55 s |
| h | 2.7:1.0 | 30 s | 2 min 20 s | 4 min 30 s |
| i | 3.0:1.0 | 30 s | 1 min 58 s | 4 min 10 s |
| j | 3.3:1.0 | 30 s | 1 min 15 s | 3 min 50 s |

Cement (f) is a low viscosity cement. Cements (g), (h), and (i) are medium viscosity cements. Cement (j) is a high viscosity cement.

Strip-shaped test bodies sized 3.3 mm×10.0 mm×75 mm were produced for the determination of flexural strength and flexural modulus of cements (f-j) in accordance with ISO 5833. Cylinder-shaped test bodies with a diameter of 6 mm and a height of 10 mm were produced for the determination of the compressive strength. A Zwick Z010 universal testing apparatus was used in the determination of the flexural strength, flexural modulus, and compressive strength in accordance with ISO 5833.

| Cement | Weight ratio of cement powder 2 and monomer liquid | Flexural strength [MPa] | Flexural modulus [MPa] | Compressive strength [MPa] |
|---|---|---|---|---|
| f | 2.2:1.0 | 66.6 ± 2.2 | 3092 ± 73 | 104.3 ± 1.1 |
| g | 2.5:1.0 | 68.8 ± 3.1 | 3204 ± 77 | 107.8 ± 1.4 |
| h | 2.7:1.0 | 74.3 ± 2.5 | 3740 ± 118 | 111.9 ± 1.4 |
| i | 3.0:1.0 | 74.2 ± 1.6 | 3627 ± 53 | 108.8 ± 3.7 |
| j | 3.3:1.0 | 72.9 ± 2.1 | 3585 ± 31 | 96.2 ± 3.2 |

ISO 5833 requires a flexural strength in excess of 50 MPa, a flexural modulus in excess of 1,800 MPa, and a compressive strength in excess of 70 MPa. The cements of examples (f-j) meet the requirements of ISO 5833 with regard to the flexural strength, flexural modulus, and compressive strength.

Figures 1A, 1B:
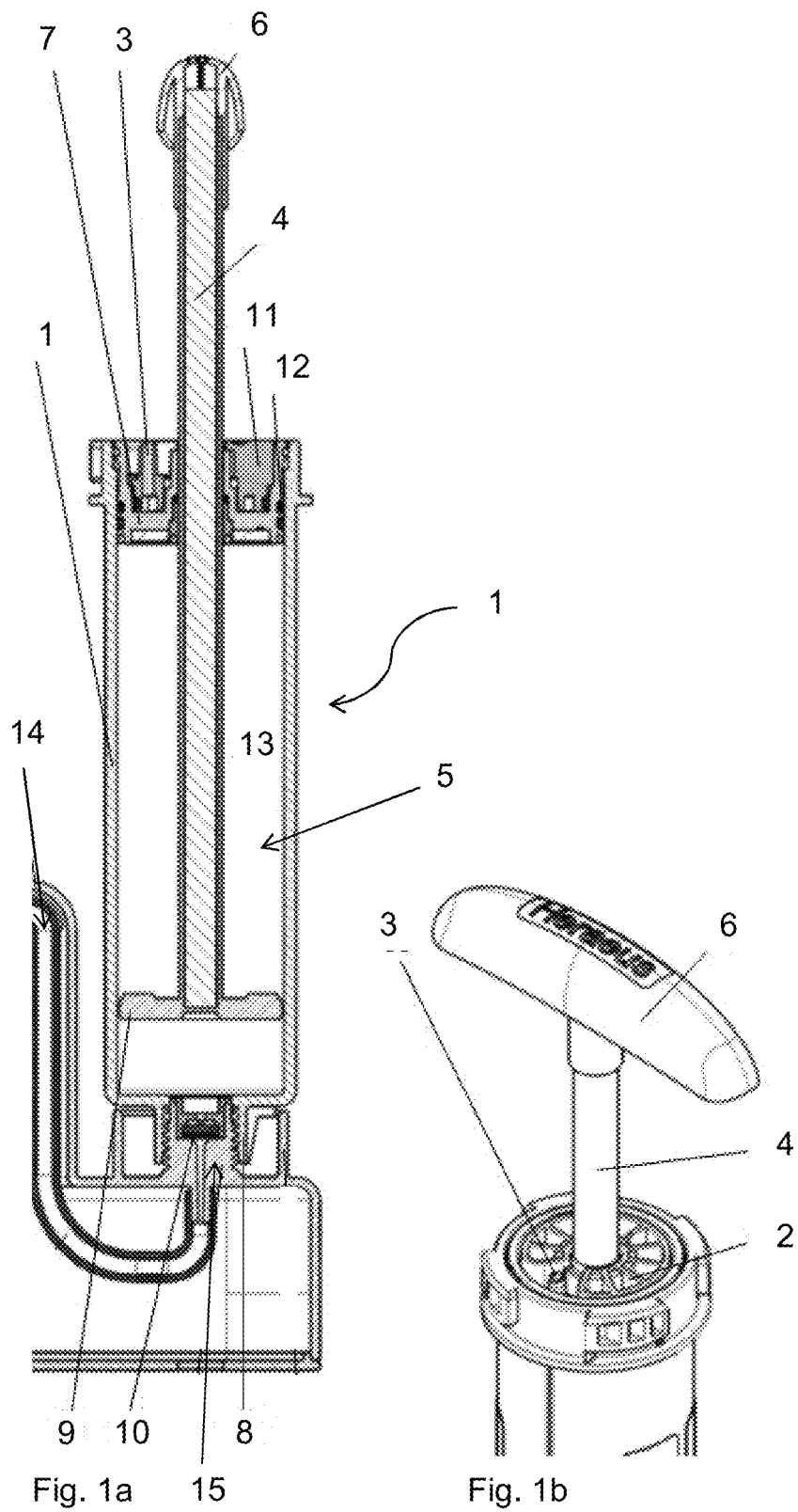
FIGS. 1a and 1b show a kit according to the invention comprising a cartridge 1 and, in particular, a disposable monomer container (vial, not shown). Further details on the design of the cartridge are evident from FIGS. 1a and 1b. The inside of the cartridge 1 is formed by a cylindrical internal space 13 that contains the cement powder. Moreover, the internal space 13 of the cartridge 1 has a mixing facility 9 consisting of multiple mixing vanes 9 arranged in it that is attached to the mixing rod 4 and can be moved in the internal space 13 by means of the mixing rod 4. Moving the mixing rod 4 allows components A and B to be mixed with each other in the mixing chamber 5. The dispensing plunger 2 has a two-part design and consists of a sterilisation plunger 7 (upper part of the dispensing plunger in FIG. 1a) and a sealing plunger 11 (lower part of the dispensing plunger in FIG. 1a) that is sealed with respect to the internal wall of the internal space 13 by means of a seal 12. The sealing plunger 11 comprises a gas-permeable, but powder-impermeable pore disc by means of which the internal space 13 can be evacuated. The dispensing plunger 2 has a cylindrical outer circumference and closes tightly against the walls of the internal space 13. The cartridge 1, in particular the cartridge connector 8, has a connecting conduit 14 allocated to it through which the monomer can be introduced into the cartridge 1 before the mixing process.

A dosing facility into which the monomer exiting from the monomer container is transferred can be arranged between the monomer container (vial) and the connecting conduit 14. The dosing facility preferably comprises a hollow cylindrical body, in which an axially shiftable plunger is arranged. The monomer can flow into or be taken up by the hollow cylinder of the dosing facility. Defined insertion of the axially shiftable plunger into the hollow cylinder comprising the monomer causes the appropriate amount of monomer for the mixing ratio according to the invention to be adjusted in the cartridge by said amount being transferred into the cartridge. The adjustment of the mixing ratio can take place by means of snap-in elements in the hollow cylinder and/or on the axial shiftable plunger.

The dispensing plunger 2 can be propelled in the internal space 13 in the direction of a dispensing opening that is arranged on the side of the internal space 13 of the cartridge 1 that is opposite from the dispensing plunger 2. Subsequently, the mixed bone cement can be expelled from the internal space of the cartridge through the dispensing opening and the dispensing tube by pressing the dispensing plunger 2 inwards, and the mixed bone cement can be applied. The expelling and applying is preceded by the cartridge 1 being detached from the connecting conduit 14 and, optionally, a cartridge bracket 15.

The features of the invention disclosed in the preceding description and in the claims, figures, and exemplary embodiments, can be essential for the implementation of the various embodiments of the invention both alone or several thereof and in any combination.

LIST OF REFERENCE NUMBERS

1 Cartridge; 2 Dispensing plunger; 3 Vacuum connector; 4 Mixing rod; 5 Mixing chamber; 6 Handle part; 7 Sterilisation plunger; 8 Cartridge connector with internal thread; 9 Mixing vane/Mixing facility; 10 Powder-impermeable and liquid-permeable filter; 11 Sealing plunger; 12 Seal; 13 Internal space; 14 Connecting conduit, 15 Cartridge bracket.

The invention claimed is:
1. A composition for use as polymerizable bone cement comprising
  (i) at least one monomer for radical polymerization comprising at least methylmethacrylate;
  (ii) at least one powdered polymethylmethacrylate-co-polymer or a powdered mixture comprising polymethylmethacrylate-co-polymers that is/are soluble in (i);
  (iii) at least one polymerization initiator; and
  (iv) at least one radiopaquer;
  wherein
  the (ii) powdered polymethylmethacrylate-co-polymer or the powdered mixture comprises at least one particulate polymethylmethacrylate-co-polymer with a molar mass Mn of more than or equal to 200,000 g/mol to less than or equal to 1,000,000 g/mol, and the at least one polymethylmethacrylate-co-polymer or the powdered mixture is obtained by polymerization of a mixture of at least 90.0% by weight of methylmethacrylate and from 1% to 10.0% by weight of one or more comonomers selected from the group consisting of at least one alkylacrylate with 1 to 5 C-atoms in the alkyl group, diene, isoprene and a mixture of said comonomers, and the total composition of (ii) accounts for 100% by weight relative to said mixture;
  wherein the composition obtained by mixing two components A and B,
  wherein component A is present as a powder and comprises
    (a.1) the at least one powdered polymethylmethacrylate-co-polymer or the powdered mixture comprising the polymethylmethacrylate-co-polymers;
    (a.2) the at least one powdered radiopaquer; and
    (a.3) the at least one polymerization initiator; and
  component B is present as a liquid and comprises
    (b.1) the at least one monomer for radical polymerization;
    (b.2) optionally, at least one polymerization accelerator; and
    (b.3) optionally, at least one stabilizer,
  wherein the weight ratio of component A to component B ranges from approximately 2.0:1.0 to 3.4:1.0 and the weight ratio is selected from
    a) less than 2.2:1.0
    b) from 2.2:1.0 to less than 3.3:1.0, or
    c) from more than or equal to 3.3:1.
2. The composition according to claim 1, wherein the at least one powdered polymethylmethacrylate-co-polymer or the powdered mixture is obtained by polymerization of at least one comonomer selected from the group consisting of the at least one alkylacrylate with 1 to 5 C-atoms in the alkyl group,
and methylmethacrylate.
3. The composition according to claim 1, wherein the component A contains 1.0 to 2.5% by weight of the polymerization initiator relative to the total composition of the component A of 100% by weight.
4. The composition according to claim 1, wherein the composition is present as
  a) low viscosity bone cement, or
  b) medium viscosity bone cement, or
  c) high viscosity bone cement.
5. The composition according to claim 1, wherein the particle size $d_{99}$ of the powdered polymethylmethacrylate-co-polymer particles is less than or equal to 100 μm.
6. The composition according to claim 1, wherein
  the composition comprises the two components A and B, wherein
  the component A is present as a powder and comprises
    (a.1) 75 to 85% by weight of at least one powdered polymethylmethacrylate-co-polymer selected from a particulate polymethylmethacrylate-co-polymer with a molar mass Mn of more than or equal to 200,000 g/mol to 1,000,000 g/mol, wherein the polymethylmethacrylate-co-polymer is obtained by polymerization of a mixture of at least 90.0% by weight methylmethacrylate and 1% to 10.0% by weight of the one or more comonomers that do not correspond to methylmethacrylate, and the total composition accounts for 100% by weight relative to said mixture;
    (a.2) 10 to 20% by weight of the at least one powdered radiopaquer;
    (a.3) 1.0 to 2.5% by weight of the at least one polymerization initiator; and
    (a.4) 0.0 to 10% by weight of at least one pharmaceutically active substance and/or pharmacologically tolerable salt thereof, wherein the total composition of components A accounts for 100% by weight; and
  the component B is present as a liquid and comprises
    (b.1) 95 to 99.9% by weight of the at least one monomer for radical polymerization;
    (b.2) 0.1 to 5% by weight of the at least one polymerization accelerator;
    (b.3) 0 to 2.0% by weight of the at least one stabilizer; and
    (b.4) optionally, a content of chlorophyllin E141, wherein the total composition of components B accounts for 100% by weight.
7. A method for producing a polymerizable bone cement by mixing two components A and B with each other, wherein the component A is present as a powder and comprises
    (a.1) at least one powdered polymethylmethacrylate-co-polymer or a powdered mixture comprising polymethylmethacrylate-co-polymers, wherein the polymethylmethacrylate-co-polymer or powdered mixture comprises at least one particulate polymethylmethacrylate-polymer-co-polymer with a molar mass Mn of more than or equal to 200,000 g/mol to less than or equal to 1,000,000 g/mol, and the at least one polymethylmethacrylate-co-polymer or the powdered mixture is obtained by polymerization of a mixture of more than or equal to 90.0% by weight of methylmethacrylate and from 1% to 10.0% by weight by weight of one or more comonomers selected from the group consisting of at least one alkylacrylate with 1 to 5 C-atoms in the alkyl group, diene, isoprene and a mixture of said comonomers, and the total composition of the at least one polymethylmethacrylate-co-polymer or the powdered mixture accounts for 100% by weight relative to said mixture;
(a.2) at least one radiopaquer; and
(a.3) at least one polymerization initiator; and
the component B is present as a liquid and comprises
(b.1) at least one monomer for radical polymerization;
(b.2) at least one polymerization accelerator; and
(b.3) at least one stabilizer;
wherein the weight ratio of component A to component B is approximately 2.0:1.0 to 3.4:1.0, and components A and B are mixed at a weight ratio selected from
a) less than 2.2:1.0,
b) from 2.2:1.0 to less than 3.3:1.0, or
c) from more than or equal to 3.3:1.0.

8. The method according to claim 7, wherein the component A contains 1.0 to 2.5% by weight of at least one polymerization initiator, relative to the total composition of the component A of 100% by weight.

9. The method according to claim 8, wherein the component A and the component B are mixed at a weight ratio of
a) less than 2.2:1.0 to produce low viscosity bone cements attaining a tack-free condition according to ISO 5833 after more than 3.0 minutes after the mixing;
b) from 2.2:1.0 to less than 3.3:1.0 to produce medium viscosity bone cements attaining a tack-free condition according to ISO 5833 after more than or equal to 1.5 to 3.0 minutes after the mixing; or
c) from more than or equal to 3.3:1.0 to produce high viscosity bone cements attaining a tack-free condition according to ISO 5833 after more than or equal to 1.0 to less than 1.5 minutes after the mixing.

10. The method according to claim 7, wherein
a defined amount of the component A, in grams, for attaining the weight ratio a), b) or c) or a volume of the component A corresponding to said amount is provided in an internal space of a cartridge, wherein the cartridge comprises a cartridge connector on one of its ends and a dispensing plunger on its other, opposite end, whereby a mixing rod is attached to or is arranged on a mixing facility on an inside of the cartridge through a feed-through, wherein the mixing facility is operated from outside by moving the mixing rod along an axis of the internal space, wherein, optionally, a connecting conduit is allocated to the cartridge, and
the component B is provided in a disposable monomer container.

11. The method according to claim 10, comprising the steps of
transferring a defined amount of the component B, in grams, for attaining the weight ratio a), b) or c) or a corresponding volume of the component B from the disposable monomer container to the cartridge (1), by means of a connecting conduit, and
mixing of the components A and B.

12. The method according to claim 11, wherein components A and B are mixed at a weight ratio of
a) less than 2.2:1.0 to obtain low viscosity bone cements attaining a tack-free condition according to ISO 5833 after more than 3.0 minutes after the mixing;
b) from 2.2:1.0 to less than 3.3:1.0 to obtain medium viscosity bone cements attaining a tack-free condition according to ISO 5833 after more than or equal to 1.5 to 3.0 minutes after the mixing; or
c) from more than or equal to 3.3:1.0 to obtain high viscosity bone cements attaining a tack-free condition according to ISO 5833 after more than or equal to 1.0 to less than 1.5 minutes after the mixing.

13. The method according to claim 11, wherein components A and B are mixed in the internal space by means of the mixing facility by operating the mixing facility by moving the mixing rod that extends into the internal space of the cartridge and is rotated and/or shifted in longitudinal direction.

14. The method according to claim 10, wherein the cartridge, containing the low viscosity, medium viscosity or high viscosity polymerizable bone cement, is being detached from the connecting conduit and the bone cement is dispensed from the internal space of the cartridge by propelling the dispensing plunger that is supported such as to be axially mobile in the cartridge and forms a boundary of the internal space of the cartridge on one side.

15. A kit for producing polymerizable bone cements, comprising component A and, optionally, component B, wherein the component A is present as a powder and comprises
(a.1) at least one powdered polymethylmethacrylate-co-polymer or a powdered mixture of polymethylmethacrylate-co-polymers, wherein the at least one powdered polymethylmethacrylate-co-polymer or the powdered mixture comprises at least one particulate polymethylmethacrylate-polymer-co-polymer with a molar mass Mn of more than or equal to 200,000 g/mol to less than or equal to 1,000,000 g/mol, and the at least one polymethylmethacrylate-co-polymer or the powdered mixture is obtained by polymerization of a mixture of at least 90.0% by weight of methylmethacrylate and from 1% to 10.0% by weight of one or more comonomers selected from the group consisting of at least one alkylacrylate with 1 to 5 C-atoms in the alkyl group, diene, isoprene and a mixture of said comonomers, and the total composition accounts for 100% by weight relative to said mixture;
(a.2) at least one radiopaquer; and
(a.3) at least one polymerization initiator; and
the optional component B is present as a liquid and comprises (b.1) at least one monomer for radical polymerization;
(b.2) optionally, at least one polymerization accelerator; and
(b.3i) optionally at least one stabilizer;
wherein the component A is present in an internal space of a cartridge, wherein the cartridge comprises a cartridge connector with an internal thread on one end and a dispensing plunger on the other opposite end, wherein a mixing rod is attached to or is arranged on a mixing facility on an inside of the cartridge through a feed-through, wherein the mixing facility is operated from outside by moving the mixing rod along an axis of the internal space of the cartridge, and, optionally, component B is contained in a disposable monomer container.

16. The kit according to claim 15, wherein at least one of the cartridge, the disposable monomer container and a dosing facility therebetween comprises markings that allow an amount of the component B to be added to attain the weight ratio or the volume ratio, that corresponds to the weight ratio, of the component A to the component B of approximately 2.0:1.0 to 3.4:1.0 to be read from the scale divisions of the marking.

17. A polymerizable bone cement obtainable by mixing the components A and B according to claim 1.

18. A polymerized cured bone cement, obtained by polymerizing the bone cement according to claim 1 in the form of spacers, or carrier material for local release of pharmaceutically active substances.

19. A method for the production of
a) low viscosity bone cements by mixing the components A and B according to claim 1 at a weight ratio of less than 2.2:1.0, wherein the bone cements attain a tack-free condition according to ISO 5833 after more than or equal to 3.0 minutes after the mixing, or
b) medium viscosity bone cements by mixing the components A and B at a weight ratio from 2.2:1.0 to less than 3.3:1.0, wherein the bone cements attain a tack-free condition according to ISO 5833 after more than or equal to 1.5 to 3.0 minutes after the mixing, or
c) high viscosity bone cements by mixing the components A and B at a weight ratio of more than 3.3:1.0, wherein the bone cements attain a tack-free condition according to ISO 5833 after more than or equal to 1.0 to less than 1.5 minutes after the mixing.

20. The composition according to claim 1 for use in vertebroplasty, kyphoplasty, and augmentation of drill holes in osteoporotic bone tissue, for filling bone cavities, for femuroplasty, for the manufacture of spacers, for mechanical fixation of articular endoprostheses, for covering skull defects or for the production of carrier materials for local antibiotics therapy, as carrier material for local release of pharmaceutically active substances.

21. The composition according to claim 1, the one or more comonomers is selected from the group consisting of at least one ethylacrylate, methylacrylate and mixtures thereof.

* * * * *